United States Patent [19]

Russel, Sr. et al.

[11] Patent Number: 5,099,837

[45] Date of Patent: Mar. 31, 1992

[54] INHALATION-BASED CONTROL OF MEDICAL GAS

[76] Inventors: Larry L. Russel, Sr., 4109 Ravine Dr., Cana Winchester, Ohio 43110; George A. Anderson, 1239A Lakeshore Dr., Columbus, Ohio 43229

[21] Appl. No.: 590,469

[22] Filed: Sep. 28, 1990

[51] Int. Cl.$^5$ .......................................... A61M 16/00
[52] U.S. Cl. ......................... 128/204.26; 128/204.18
[58] Field of Search ..................... 128/204.18, 204.21, 128/204.22, 204.23, 204.24, 204.25, 204.26

[56] References Cited

U.S. PATENT DOCUMENTS

| | | | |
|---|---|---|---|
| 2,830,580 | 4/1958 | Saklad | 128/29 |
| 3,097,638 | 7/1963 | Streimer | 128/2.07 |
| 3,333,584 | 8/1967 | Andreasen | 128/145.5 |
| 3,357,428 | 12/1967 | Carlson | 128/145.8 |
| 3,611,178 | 10/1971 | McConnell | 331/65 |
| 3,659,598 | 5/1972 | Peters | 128/145.8 |
| 3,736,949 | 6/1973 | Wolter | 137/102 |
| 3,820,539 | 6/1974 | Ollivier | 128/145.8 |
| 3,831,596 | 8/1974 | Cavallo | 128/145.8 |
| 3,834,382 | 9/1974 | Lederman | 128/145.8 |
| 3,863,630 | 2/1975 | Cavallo | 128/145.6 |
| 3,889,669 | 6/1975 | Weigl | 128/145.8 |
| 3,910,270 | 10/1975 | Stewart | 128/145.8 |
| 3,952,740 | 4/1976 | Scurlock | 128/145.8 |
| 3,976,064 | 8/1976 | Wood | 128/145.8 |
| 4,054,133 | 10/1977 | Myers | 128/142.2 |
| 4,057,059 | 11/1977 | Reid | 128/145.8 |
| 4,106,503 | 8/1978 | Rosenthal | 128/194 |
| 4,120,300 | 10/1978 | Tiep | 128/203 |
| 4,121,579 | 10/1978 | Bird | 128/145.8 |
| 4,141,354 | 2/1979 | Ismach | 128/145.6 |
| 4,141,356 | 2/1979 | Smargrassi | 128/145.8 |
| 4,186,737 | 2/1980 | Valenta | 128/203.28 |
| 4,197,843 | 4/1980 | Bird | 128/200.14 |
| 4,206,754 | 6/1980 | Cox | 128/204.21 |
| 4,215,681 | 8/1980 | Alkin | 128/204.21 |
| 4,241,732 | 12/1980 | Berndtsson | 128/204.24 |
| 4,281,651 | 8/1981 | Cox | 128/204.23 |
| 4,289,126 | 9/1981 | Seireg | 128/204.24 |
| 4,289,142 | 9/1981 | Kearns | 128/716 |
| 4,316,182 | 2/1982 | Hodgson | 340/606 |
| 4,323,064 | 4/1982 | Hoenig | 128/204.21 |
| 4,381,774 | 5/1983 | Schreiber | 128/202.22 |
| 4,393,869 | 7/1983 | Boyarsky | 128/204.18 |
| 4,414,982 | 11/1983 | Durkan | 128/716 |
| 4,457,303 | 7/1984 | Durkan | 128/204.24 |
| 4,461,293 | 7/1984 | Chen | 128/204.23 |
| 4,462,398 | 7/1984 | Durkan | 128/200.14 |
| 4,484,578 | 11/1984 | Durkan | 128/204.24 |
| 4,519,387 | 5/1985 | Durkan | 128/204.23 |
| 4,706,664 | 11/1987 | Snook | 128/204.23 |
| 4,909,246 | 3/1990 | Kiske et al. | 128/205.17 |
| 4,971,049 | 11/1990 | Rotariu et al. | 128/204.21 |

Primary Examiner—Edgar S. Burr
Assistant Examiner—Stephen R. Funk
Attorney, Agent, or Firm—Mueller and Smith

[57] ABSTRACT

Method and apparatus are described for supplying medical gas such as oxygen to patients through flexible conduiting terminating in a cannula. Pulses of select duration of the oxygen are supplied in response to the negative pressure associated with a detected patient inhalation. Following the supply of a given pulse, the apparatus dwells for a predetermined interval, for example 0.6 seconds, whereupon a next pulse is supplied if inhalation continues. The first pulse supplied in response to any negative inhalation pressure has a quantity corresponding with a prescribed oxygen flow. Thus, subsequent pulses may supply oxygen ambulatory activities of the patient. The apparatus includes a triggering suppression feature avoiding the false pulsing effects otherwise occasioned by pneumatic transients generated by the pulsing technique. Additionally, a pulse triggering sensitivity which is manually adjustable is incorporated with the control circuit of the apparatus. Improved battery charging and stand-by continuous flow circuit metering is incorporated with the apparatus.

29 Claims, 5 Drawing Sheets

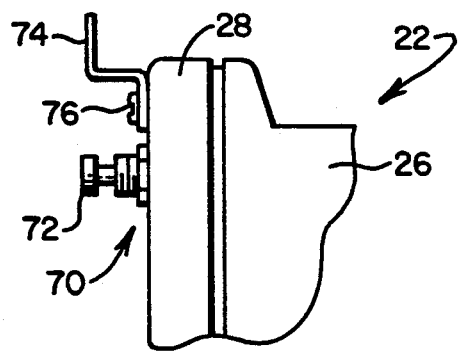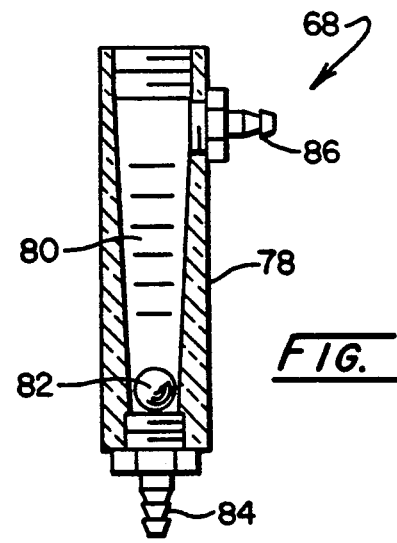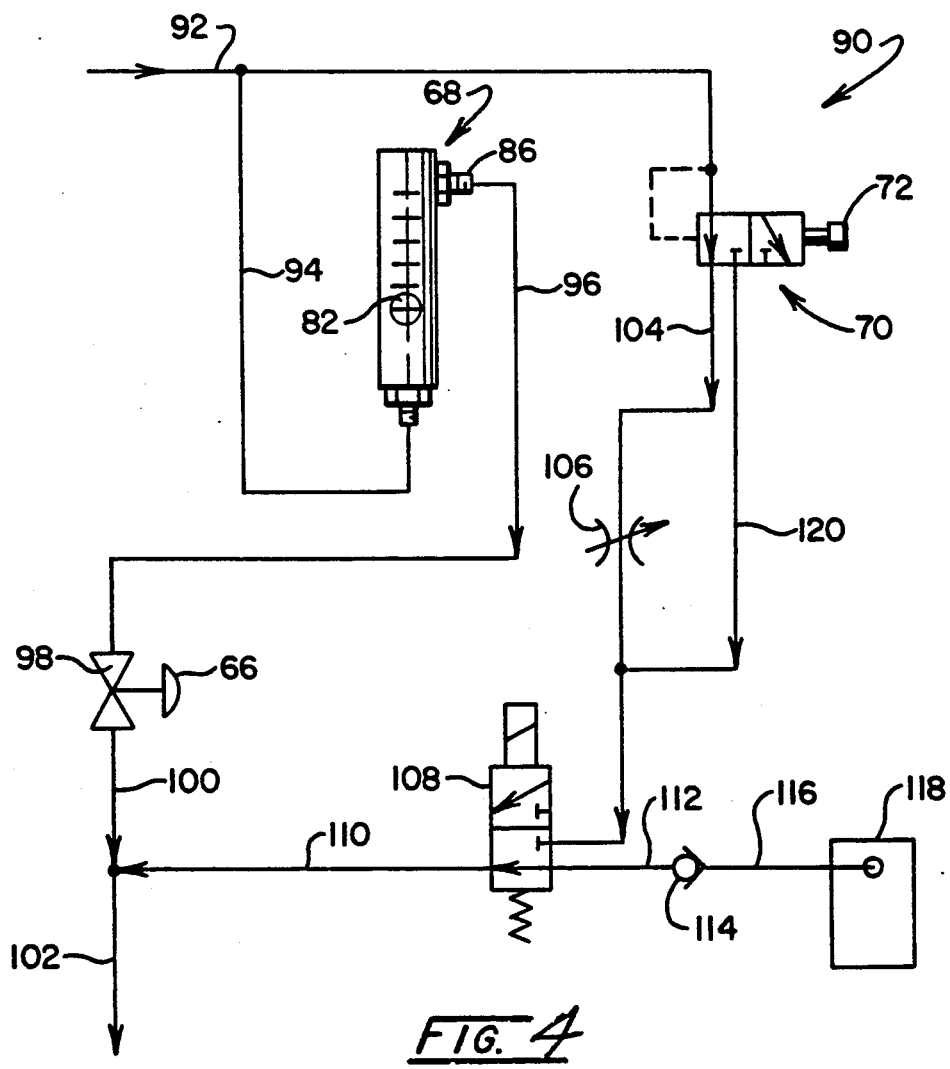

INHALATION-BASED CONTROL OF MEDICAL GAS

BACKGROUND OF THE INVENTION

The administration of supplemental oxygen is well established form of therapy for patients with chronic respiratory difficulties. For example, oxygen is administered not only to those patients with chronic obstructive lung disease who are hypoxemic, but also to patients with pulmonary insufficiency caused by such disorders as interstitial lung disease, sleep apnea, and kyphyoscoliosis. Conventionally, the administration of prescribed supplemental oxygen has been on a continuous basis, the flow of oxygen not being interrupted, and the medical profession has adapted a general technique for prescribing such therapy typically by specifying the gas application in terms of continuous flow, for example 3 liters per minute or the like.

Continuous, long-term oxygen therapy is expensive, a substantial portion of the gas being wasted. In this regard, approximately one-third of the respiratory cycle is spent in inhalation and two-thirds in exhalation. Thus, a device that delivers oxygen during inspiration only while assuring adequate alveolar gas exchange will serve to conserve the gas, while prolonging the duration of a given supply. Those supplies, of course, may be derived from generally immobile oxygen concentrators, liquid oxygen systems, or large oxygen cylinders. Lowering the gas demands for a given patient, in turn, evokes savings in the transportation and operation of such supplies. Recognizing the inefficiencies of continuous oxygen therapy, investigators have looked to respiratory-phased or responsive systems wherein oxygen is, in effect, pulsed to the patient under a control logic based upon the physician prescribed gas flow rate and the breathing characteristics. One such breathing characteristic adduced in the course of investigation has been that the initial 60% of any inspiration time is devoted to the introduction of "fresh" gas into the alveoli. Gas introduced for the remaining 40% of a given inspiration essentially has no oxygen transfer effect and represents what has been referred to as "dead-space" ventilation. See generally:

"Efficacy of Pulsed Oxygen Delivery During Exercise" by McDonnell, Wanger, Senn and Cherniack, *Respiratory Care*, vol. 31, No. 10, Oct. 1986.

"Oxygen Conserving Devices" by O'Donahue, Jr., *Respiratory Care*, vol. 32, No. 1, Jan., 1987.

"Efficacy of he Oxymizer Pendant in Reducing Oxygen Requirements of Hypoxemic Patients, by Gonzales, Huntington, Romo, and Light, *Respiratory Care*, vol. 31, No. 8, Aug., 1986

"Oxygen Transport and Utilization", by Dantzker, *Respiratory Care*, vol. 33, No. 10, Oct., 1988

"Pulmonary Responses to Exercise", by Lough, *Respiratory Care*, vol. 34, NO. 6, June, 1989.

"The Future of Home Oxygen Therapy", by O'Donohue, Jr., *Respiratory Care*, vol. 33, No. 12, Dec., 1988

Any approach to controlled oxygen administration also should account for the lifestyle and emotion driven characteristics of the patient. Typically, this patient initially will be prone to panic mentally in consequence of an apprehension of perceived suffocation. The normally-encountered response is a rapid breathing rate, for example about 20 breaths per minute, and a breathing technique which is described as "shallow", typically exhibiting a rapid or gasping commencement of inhalation. Notwithstanding the mentally induced difficulties leading to strained breathing patterns, breathing becomes problematic to the patient when transitioning from a rest on an ambulatory or moving activity, inasmuch as the body imposes a heightened oxygen demand which was not present in a rest condition. As a consequence of this increased demand resulting from even minor movement, patients have a natural tendency not to carry out even the most menial or basic of activities to exacerbate the requirements for their care. One approach of therapists has been to train the patient to breathe more slowly and deeply to improve oxygen uptake efficacy. For example, patients undergoing pulmonary rehabilitation may be taught a breathing routing while walking wherein inspiration time extends over an interval of two steps and expiration time extends for three steps. During this exhalation time the lips are pursed to form a positive pressure. Therapists have been observed to instruct the patient to "smell the roses" in describing this form of training exercise. Such categorizations as well as others are employed to cause the patient to remember to breathe in a trained manner. When the patient forgets, the apprehension again sets in with attendant anxiety and return to fast paced shallow breathing.

In view of the foregoing, it is desirable that any respiration phased or pulsed oxygen delivery system aid in the very procedure of training the patient to breathe under optimal self-control. The gas delivery approach, while achieving a desired gas concentration, should also provide a basic physician prescribed oxygen flow rate, e.g. in liters per minute, but also accommodate unschedulated ambulatory activity with temporary, higher gas transfer rates, and without resort to manual mechanical valve changes and the like. Where such patient activity increases with attendant increased oxygen demand, the pulse based delivery systems should retain a capability for temporarily exceeding prescribed oxygen delivery rates during patient activity excursions. Following such excursions and the development of patient rest-based breathing stability, the gas delivery rate should return to physician prescribed levels without resort to manual procedures. Throughout all such gas exchange alterations, the patient should receive perceptible cuing that all is in order and requisite oxygen is available. With such cuing, patient apprehension which otherwise may be experienced, is more readily dispelled to the overall comfort and confidence of that individual.

The implementation of this desirable respiratory phase oxygen administration has posed a variety of technical problems to equipment designers. For example, systems carrying out pulse oxygen delivery based upon detecting negative inhalation pressure occurring during a breathing cycle should employ highly sensitive pressure sensing devices. Typically, these sensors utilize a diaphragm-actuated wheatstone bridge configuration which provides an output transitioning from a balance to an unbalance condition in response to patient inspiration. Over periods of time and with temperature transitions, these devices tend to drift or become unbalanced, leading to erratic or insensitive performance. Where the sensors are used in geographic regions of high altitude, their sensitivity may be severely impaired. Thus, some form of response adjustment which is simple for the user is desired.

Where a desired high sensitivity to negative inhalation pressure is achieved, erratic pulse system behavior also is experienced due to pneumatic transients which are developed within gas delivery conduits as an oxygen supply pulse interval terminates. Often, the system will react to these transients by generating uncontrolled, noise-induced pulses, a phenomenon sometimes referred to as "autopulsing".

Because the pulsing valve systems generally are actuated by the energization of current-demanding windings of solenoid valves, any desired utilization of rechargeable batteries with the system is rendered difficult. Often, even though recharging networks are supplied, these networks are incapable of bringing rechargeable battery sources back to optimum voltage levels. The system also should incorporate techniques for diverting from a controlled pulse actuated supply of medical gas to a continuous flow. Such switch-over to a different gas flow path may be occasioned, for example, with loss of power or for applications, for example, requiring the nebulized applications of medicaments. While valving for carrying out such procedures is readily available, a small, inexpensive and practical form of flow metering for such alternative utilization of the application systems has been elusive to designers. Finally, the devices employed for oxygen application generally have been restricted to the outputs of only certain forms of gas pressure regulators. It will be desirable to provide control devices which may perform with more than one regulated gas supply input.

SUMMARY

The present invention is addressed to apparatus and method for supplying medical gas to the respiratory function of a patient wherein a pulsing technique is employed meeting prescribed, at rest oxygen requirements, as well as the increased support requirements of ambulatory or patient physical activity. In addition to accommodating these desired therapeutic concerns, the pulsing technique of oxygen administration serves to aid in training patients undergoing pulmonary rehabilitation. For example, as the patient breathes slower and deeper, additional pulses of oxygen are delivered and this delivery is accompanied by tactile, aural and visual cuing. The medical gas pulse is sharply defined such that it is felt by the patient as it emerges from a cannula. The formation of the pulse is carried out in a manner providing a sharp "click" sound and a light is flashed. Thus, the patient is encouraged to breathe therapeutically and is assured that pulmonary treatment is under way. Improvements also are witnessed in the control apparatus of the invention wherein a highly sensitive approach to the sensing of the negative pressures of patient inhalation is achieved in avoidance of the dilatory effects of pneumatic transients which necessarily will occur in the delivery conduiting. In effect, the triggering output of the apparatus is suppressed for a predetermined interval following the termination of the interval of a pulse which defines a medical gas output. It is this same interval which, upon the removal of suppression procedures, permits a next or second pulse procedure to be carried out, for example, within 0.6 seconds of the ending of the next previous pulse. Employing a diaphragm actuated bridge type pressure sensor, the outputs of which transition from a balance to an unbalanced condition to sense negative pressure, the apparatus of the invention achieves a unique sensitivity or response adjustment which may be applied by the user. Thus, the drifting effects of pressure sensors can be accommodated for quite readily and, for example, the devices may be employed within territories of varying altitudes and air density. Improvements also are achieved with the apparatus in the development of battery charging and the selection of pulse intervals.

Another feature of the invention provides a method for supplying medical gas to the respiratory system of a patient during the course of inhalation and exhalation comprising the steps of:

providing a supply of the gas under regulated pressure;

providing a gas conduit input positionable upon the patient and responsive to the instantaneous pressures of the patient respiratory system to exhibit a negatively categorized pressure upon inhalation;

detecting the commencement of a negatively categorized pressure;

providing a first pulse supply of predetermined duration of the gas to the patient in a quantity corresponding with a select gas application rate, substantially at the detected commencement of negatively categorized pressure; and providing a second pulse supply of predetermined duration of the gas to the patient in the continued presence of the negatively categorized pressure and following a first predetermined delay interval.

Another feature of the invention provides apparatus for administering medical gas from a source thereof to the respiratory tract of a patient in correspondence with a select application rate. The apparatus includes a medical gas circuit connectable with the source and having a gas application valve actuable for a pulse forming interval to apply the medical gas to the patient through an application conduit conveying an inhalation and expiration pressure condition of the patient. A pressure sensor is coupled with the medical gas circuit and has a sensing output in response to the presence of an inhalation pressure condition through the application conduit. An amplifier responds to the sensing output for deriving an amplified sensing signal and a comparator is responsive to a threshold input of predetermined level and to the amplified sensing signal for deriving a triggering output in correspondence with the inhalation pressure condition. A pulse timer responds to the trigger output for deriving a pulse output of select duration for effecting the actuation of the gas application valve for the select duration and a next pulse timing arrangement responds to the pulse output for effecting the derivation of the trigger output a predetermined interval subsequent to the pulse output in the presence of the sensing output.

Another feature of the invention provides apparatus for administering medical gas to the respiratory tract of a patient. The apparatus includes a medical gas conduit or circuit having a gas application valve actuable to apply the medical gas to the patient through an application conduit in response to a negative inhalation pressure from the patient. A pressure sensor is coupled with the medical gas circuit and has a sensing output in response to the negative pressure. An amplifier is provided having an output of first stand-by level and responsive to the sensing output to alter the stand-by level to a negative pressure sensing level signal. A comparator is responsive to a threshold input of predetermined level and to the negative pressure sensing signal exceeding the threshold level for deriving a triggering output. A sensitivity adjustment network is provided which is manually adjustable to vary the amplifier stand-by level away from or towards the comparator threshold level and a pulse timer is responsive to the triggering output for deriving a pulse output of select duration for effecting actuation of the gas application valve.

Another feature of the invention provides apparatus for administering medical gas from a source thereof at source pressure to the respiratory tract of a patient. The apparatus includes a solenoid valve having a winding energizable to assume a gas transfer orientation from a closed orientation. A first gas transfer path is provided which is connectable with the source and in gas transfer relationship with the valve. A by-pass valve is provided which is manually adjustable to provide select gas flow rates. A second gas transfer path is connectable with the source and in gas transfer relationship with the by-pass valve. A third gas transfer path is connected in gas transfer relationship to the by-pass valve and the solenoid valve and is operably associated with the patient respiratory tract. A variable area gas flow meter is provided including a transparent tubular housing, a ball therein responsive in gas buoyancy to fluid flow through the housing, and gas flow rate indicia provided on the housing, the device being coupled within the second gas transfer path; and a control arrangement is provided for selectively energizing the solenoid winding.

Another feature of the invention provides apparatus for administering medical gas to the respiratory tract of the patient. The apparatus includes a medical gas circuit having a solenoid valve energizable to open the valve with a winding to apply a pulse of medical gas to a patient through an application conduit. A pressure sensor is operatively associated with the application conduit and has a sensing output in response to the breathing condition of the patient. An amplifier is provided which is responsive to the sensing output for deriving a sensing signal and a timing control circuit responds to the sensing signal for energizing the solenoid valve winding for predetermined pulse intervals. A rechargeable battery is provided as well as an arrangement connectable with an internal source of electrical power for providing a d.c. input source. The voltage regulator is provided having an input connected with the d.c. input source and also has an output. An impedance network is provided which is switchable between first and second impedance configurations. A switch arrangement is provided having an off orientation establishing the impedance network first impedance configuration for applying a long term level charge current to the battery from a regulator output, and has an on orientation for deriving the second impedance configuration supplying current from a common output to the winding from the regulator output and battery during the energization of the winding and functions to recharge the battery when the winding is not energized.

Other objects of the invention will, in part, be obvious and will, in part, appear hereinafter. The invention, accordingly, comprises the apparatus and method possessing the construction, combination of elements, arrangement of parts and steps which are exemplified in the following detailed disclosure.

For a fuller understanding of the nature and objects of the invention, reference should be had to the following detailed description taken in connection with the accompanying drawings.

BRIEF DESCRIPTION OF THE DRAWINGS

FIG. 2 is a partial side view of control apparatus depicted in FIG. 1;

FIG. 3 is a partial sectional view of a flow meter incorporated with the control apparatus revealed in FIG. 1;

FIG. 4 is a schematic diagram of the pneumatic control components incorporated within a control component shown in FIG. 1;

DETAILED DESCRIPTION OF THE INVENTION

The unique operational approach of the apparatus of the invention permits its use in evolving a method for training patients requiring oxygen administration in controlling their pulmonary activities. Because of the pulsing program of the apparatus, the patients also are automatically provided additional oxygen at quantities above those prescribed at rest when they become ambulatory or move about. Typically, an increase in dosage of one liter per minute is prescribed for ambulatory activity. However, while the patient is ar rest, the apparatus provides the flow rate of oxygen which is prescribed by the attending physician. Because of the uniqueness of the pulse control program, it also will be observed that the approach taken by the invention permits the apparatus incorporated therewith to be employed in other medical uses with other medical gases. In this regard, the apparatus will find immediate utility in connection with the administration of anesthetic categorized gases such as nitrous oxide used in fields such as dentistry.

Figure 1:
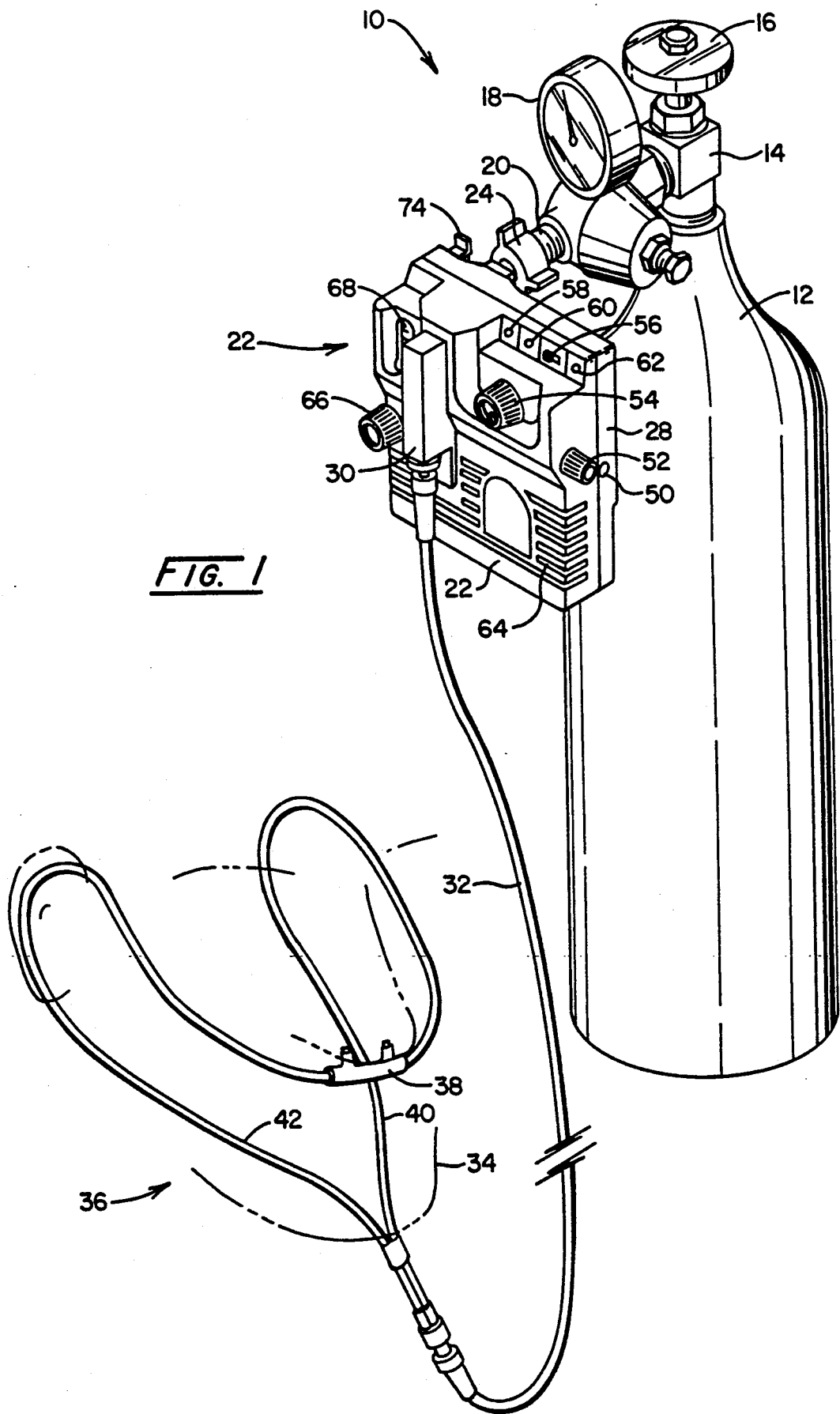
FIG. 1 is a perspective representation of a respiratory based medical gas delivery system according to the invention.

Looking to FIG. 1, a respiratory based medical gas delivery system is represented in general at 10. In the discourse to follow, the gas involved will be referred to as oxygen, however, it may be understood that other medical gases may be considered for use with the method and apparatus of the invention. The system 10 is seen to incorporate a source of oxygen as represented by the oxygen cylinder 12. Cylinder 12 is seen accessed by an open-close valve 14 which is actuated by the knob 16. Coupled to the output of valve 14 is a regulator 18 which functions, for example, to reduce the tank pressure of the gas and cylinder 12 to a system pressure, for example of 50 psig. Depending upon custom, this value may change, for example, a regulation to 20 psig may be called for. This regulated supply gas output is then presented via externally threaded conduit 20 to the input of a control apparatus according to the invention and represented in general at 22. Connection between the input to apparatus 22 and conduit 20 is by a hand actuable coupling nut 24. Nut 24 is seen to have winged protrusions thereon to facilitate the hand tightening of its connection with conduit 20.

Apparatus 22 is formed of a two-component housing, the forward component thereof being represented at 26 and the corresponding and mated component being represented at 28. Extending from the forward component 26 is an oxygen delivery output port 30 to which is connected an elongate and flexible polymeric application conduit 32. Conduit 32 may have a length, for example, extending to 30 feet to permit movement by the patient, the head of which is partially schematically represented by a dashed line 34. Conduit 32 is seen to be coupled to a cannula assembly represented at 36 which includes a dual ported cannula 38, the ports of which are insertable within the patient's nostrils and which is coupled to dual flexible polymeric lines 40 and 42 which flex around and are supported from the ears of the head 34 of a patient. Thus, the patient need not hold the cannula 38 in the nostril accessing orientation shown.

Apparatus 22 incorporates a rechargeable battery and provides access to an external electrical power input at connector 50 within housing component 28. Adjacent to the connector 50, there is an adjustment knob 52. Knob 52 may be adjusted by the patient or attendant to alter the response or sensitivity of the apparatus 10 to create pulses of delivered oxygen. The adjustment provided by this knob is of particular value in conjunction with the use of apparatus 22 at geographic locations of higher elevation and correspondingly thinner or lower pressure air mass. Next across the apparatus 22 is a dosage control knob 54. Knob 54 is detect adjustable to provide for setting the prescribed flow rate or dosage in liters per minute. This dosage may range, for example, through 12 positions, each representing a one-half liter per minute increment of application of medical gas. In accordance with the invention, prescribed liters per minute are equivalent to pulses per minute for evaluating gas quantities administered. Above the knob 54, within housing component 26, are located an on/off switch 56, a low battery visual output 58. This output may, for example, be provided as a light emitting diode (LED). Adjacent the diode 58, there is provided a pulsing indicator 60. Indicator 60 may be provided, for example, as an energized LED and will been seen to be energized during each pulse output of oxygen to the patient. Thus, a visual cue is given to the patient that oxygen is being supplied for that pulse interval. Finally, a visual apnea alarm is provided at 62. This alarm output may be provided, for example, as an LED. In general, this alarm will be activated following an interval of 70 seconds wherein no breathing is detected by the apparatus 22. Along the lower portion of housing component 26 there is seen to be an open grill structure 64. This open grill structure provides for facilitating two acoustic outputs. In particular, the first output is an aural cuing one which permits the patient to aurally hear the abrupt "click" sound occasioned by pulsing of gas to the cannula 38. The audible cue is employed as an assurance to the patient that oxygen is coming and functions to aid in the control of panic-driven rapid short breathing conditions. Additionally positioned behind the pen grill 64 is a piezoelectric driven alarm device (not show) which is activated in conjunction and simultaneously with the activation of apnea alarm output 62.

On the opposite side of port 30 there is located an adjustment knob 66 which performs in conjunction with a tubular shaped variable area meter (Rotameter) 68. The knob 66 and meter 68 form a bypass control for providing a continuous flow of gas at a selected rate of flow form port 30. This bypass function may be resorted to, for example, in the vent of a low battery or circuit failure. For such situations, the system can be switched over to the prescribed dosage with appropriate adjustment of knob 66. The continuous flow feature also may be used, for example, for nebulizer-based treatment where a bronchial dilator is required as part of the administration of medical gas to the patient.

Referring to FIG. 2, a partial representation of the upper right portion of rear component 28 of apparatus 22 is revealed. This portion of the apparatus 22 includes a plunger actuated valve represented in general ay 70 and shown having an outwardly biased plunger 72 which, in the normally outwardly biased state, provides for operation of apparatus 22 in conjunction with a 50 psig gas input. Alternately, plunger 72 may be depressed and the L-shaped clip 74 attached to component 28 by screw 76 may be rotated to hold plunger 72 inwardly. When in that orientation, the valve 70 provides pressure reduction for application of 20 psig gas. The particular valve which may be employed for this purpose may, for example, be a sub-miniature 3-way valve No. SMAV-3 produced by Clipparde Corporation.

Looking to FIG. 3, the variable area meter 68 is revealed at a higher level of detail. Meter 68 is formed having an internally tapered transparent tube 78 with graduated indicia as at 80 formed thereon. A small steel ball 82 is positioned within the tube 78 and an input connector 84 is situated at the bottom thereof while an output connector 86 is positioned at its upper end. The device 68 is mounted vertically in use and the rate of passage of gas through conduit 84 and out of conduit 86 adjusts the buoyancy and thus, elevation of ball 82 in accordance with flow rate.

Referring to FIG. 4, a pneumatic diagram of the gas flow control components of apparatus 22 is revealed in general at 90. The input to the system is represented at line 92 which, for operation of device 22 in a manual or continuous flow mode is seen coupled to path line 94 and the input connector 84 of variable area meter 68. The pneumatic flow passes through meter 68 and from connector 86 and path line 96 to one side of a rate adjustment valve, the flow rate through which is controlled by knob 66. The circuit then continues as represented at path line 100 to the output of device 22 as represented at line 102.

Now considering the electronic controlled output of the flow control system 90, input line 92 also is seen to be directed to one input of three-way valve 70 having the earlier-described plunger actuator 72 which is biased outwardly to provide the valve configuration symbolically represented. In such orientation, gas flow from line 92 passes through valve 72 to gas transfer path line 104 whereupon the flow is adjusted by an internally disposed variable regulator 106 which functions to facilitate factory calibration. Line 104 then continues to the input of a solenoid actuated valve 108. Valve 108, provided, for example, as a type 11-16-3BV-5 marketed by Pneutronics, Inc., is spring-biased to the orientation shown wherein an open path is made from output line 102, line 110 extending therefrom to valve 108, from valve 108 via line 112 to one input of a check valve 114. The opposite side of check valve 114 is coupled via line 116 to a vacuum or negative pressure detector 118. With this stand-by or normal orientation, an inhalation on the part of the patient having the cannula as at 38 placed in operating nostril insertion orientation, will be sensed through check valve 114 at device 118. Check valve 114, which may be provided, for example, as a type AL F2804402 marketed by Air Logic Corp. prevents damage to device 118 on the occasion of a high pressure excursion or transient at the input 102 as generated from pulsing or by such phenomena as a sneeze or the like. Upon the excitation of the winding of the solenoid at valve 108, the valve applies gas under pressure from line 104 to lines 110 and 102 for a predetermined short pulsing interval. The actuation of valve 108 is with full power from the electrical source available and is sharp or efficient exhibiting a high rising time, as it were, in opening and a similarly rapid fall or closing time. As a consequence, a well defined pulse of oxygen under pressure is formed which passes through lines 110 and 102 to the patient. The patient physically feels this pulse at the nostril and is thus assured that oxygen has entered the respiratory system. This tactile "feel" of the application for administration of oxygen is valuable in both the training of the patient in proper clinical based breathing as well as in ameliorating the apprehension encountered by patients typically in learning the technique of proper breathing for the lung or respiratory condition at hand. In addition the tactile cuing achieved with the operation of valve 108, the device, so actuated, makes a pronounced clicking sound which is readily perceptible and is made available to the surround or environment of apparatus 22 by virtue of the openings of grill 64 (FIG. 1). Thus, from the electrically and mechanically efficient operation of solenoid actuated valve 108 both a tactile and an acoustic cuing is made deliverable to the patient.

Where plunger 72 of valve 70 has been depressed and retained in position, for example by clip 74 (FIG. 2) then input line 92 is coupled through valve 70 to line 120 and hence to line 104 and valve 108 for operation in the manner described hereinabove.

Figure 5:
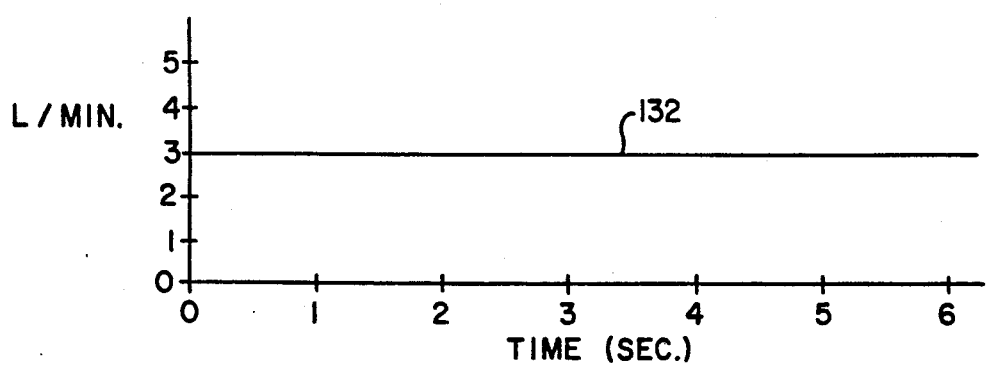
FIG. 5 is a graph showing gas delivery rates in liters per minute versus time of delivery in seconds.

Turning to FIG. 5, a representation of a continuous flow of oxygen at a prescribed rate of 3 liters per minute is represented by 132. Curve 132, for example, typifies the utilization of the continuous flow aspect of apparatus 22 as represented in FIG. 4 by lines 96, 100, and valve 98.

Figure 6:
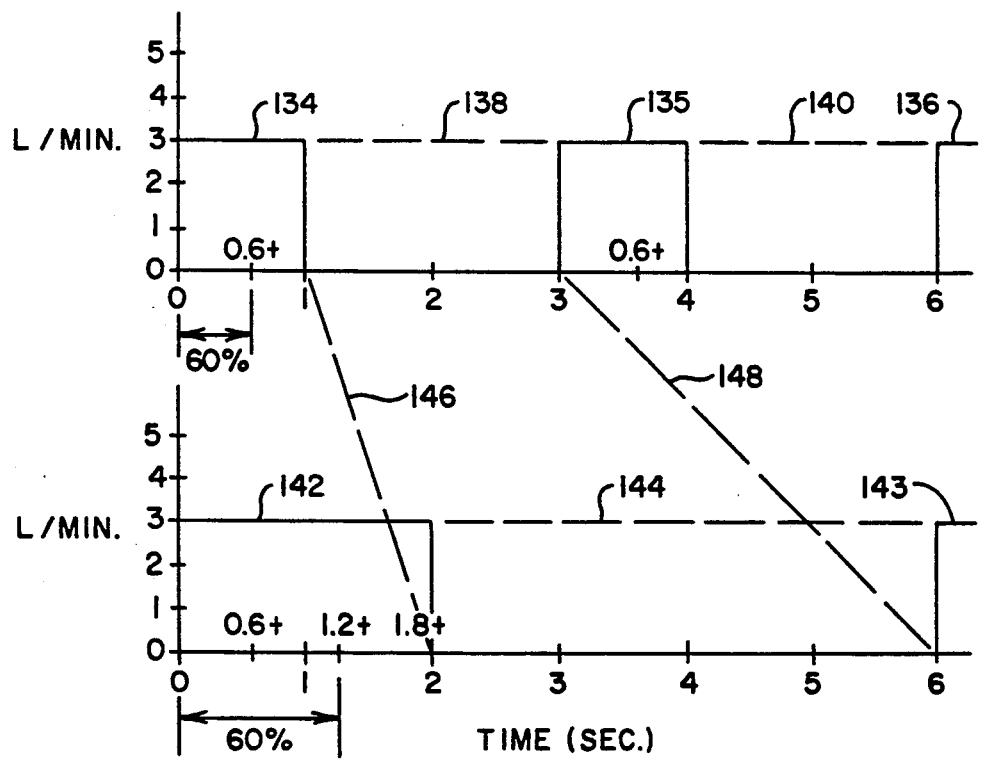
FIG. 6 shows two medical gas delivery graphs, the upper identifying a breathing rate of 20 breaths per second while the lower associated graph shows medical gas delivery in conjunction with a breathing rate of 10 breaths per minute, dashed line interconnections showing intermediate values.

Looking to FIG. 6, a representation of a breathing pattern corresponding with 20 breaths per minute of the patient is provided. In the curve, the inhalation or inspiration stage of such breathing is represented by successive block-shaped regions 134–136. A total breath profile including inhalation is represented at region 134 and corresponding exhalation is represented by the adjacent dashed component 138 similarly, exhalation region 140 follows inhalation region 135. A full breath is seen to encompass a total period of three seconds. Of the inhalation period, investigators have determined that 60% of any given inhalation interval as represented by the region 134 is effective for the introduction of oxygen into the alveoli. The remaining 40% of the inhalation is sometimes referred to as "dead-space ventilation" wherein the ingested air essentially remains idle within the respiratory tract. Under the method of the present invention, a pulse of oxygen is supplied to the patient at the commencement of inhalation and that pulse represents a quantity of oxygen corresponding with a prescribed dosage rate, for example as shown in the graph of FIG. 6, a rate of 3 liters per minute. As noted earlier, the inhalation and expiration represented at regions 134 and 138 is at a rate considered "panic" or shallow breathing. In accordance with the method of the invention, the patient, while inspiring, as represented at region 134 also will receive a second pulse of oxygen of equal quantity as the first pulse following an interval of six-tenths of one second from the first pulse. Thus, the position 0.6+ (0.6 seconds plus pulse interval) is represented within region 134. During excited, labored, or apprehensive breathing patterns, the patient will receive a reassuring second pulse of oxygen and, as noted earlier herein, will not only tactiley feel the generation of the pulse but will hear its generation and may observe its existence by the illumination of an LED 60 (FIG. 1). In general, the duration of the first and second pulse supplies of oxygen will be at least about 128 ms. This same operation then reoccurs in conjunction with the inspiration represented at region 135 for the next breath as well as the inspiration as commencing with region 136. Controlled breathing of the patient, for example at 10 breaths per minute, is represented by the inspiration region 142–143 of FIG. 6. This inhalation at region 142 is seen to encompass two seconds of a total breathing time including inhalation region 142 and exhalation or expiration region 144. Note, however, that the technique of the invention provides an initial pulse at the commencement of inhalation or time zero having a quantity of oxygen equivalent to an application of 3 liters per minute. This is applied by pulse, again giving the cuing symbols to the patient described above. As this initial inhalation continues, delay ensues of about 0.6 seconds, whereupon a next or second pulse preferably of the same oxygen quantity is executed. Again, the patient feels, hears, and sees the cuing associated with that second pulse. Because of the 2 second interval of this inhalation, a third pulse is experienced following another delay of 0.6 seconds or at about 1.2 seconds plus accumulated pulse intervals. Finally, for this therapeutically trained form of inhalation, the patient may receive still another pulse with attendant cuing at just over about 1.8 seconds of the initial. In general, it may well be observed that the 0.6 second intervals occur following the completion of each pulse, such that an accumulation of pulse duration time is presented. However, the first and second pulses of oxygen provided during this inhalation region 142 are effective substantially only during the first 60% of region 142. The third pulse, in effect is one providing reassurance to the patient, encouraging the form of breathing shown.

Another aspect of the type breathing involved is in connection with movement or ambulatory activity of the patient. Where such movement is undertaken under trained breathing conditions, then the additional oxygen becomes available to the patient encouraging the patient to carry out such movement. Breathing rates intermediate those represented by the top graph and the bottom graph of FIG. 6 are illustrated by the dashed interconnecting lines 146 and 148.

Figure 7:
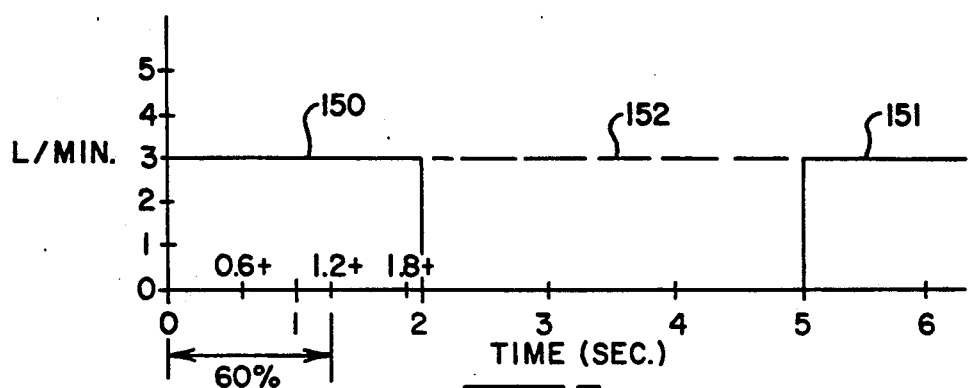
FIG. 7 is a graph representing medical gas delivery in liters per minute versus time and depicting a breathing rate of 12 breaths per minute.

Referring to FIG. 7, a patient breathing rate of 12 breaths per minute is illustrated. This rate represents the results of pulmonary rehabilitation and resultant controlled breathing on the part of the patient. During that period of time, it may be observed that in the longer, training induced 2 second period of inhalation represented at regions 150 and 151, three pulses will be delivered under the method at hand. The expiration period then is represented, for example, by the region at dashed line 152. Here again, the tactile or pulse impact, aural and visual cuing afforded by the technique of the invention causes the patient to think of proper breathing procedures and encourages the patient to breath more deeply and thus more slowly.

Figure 8:
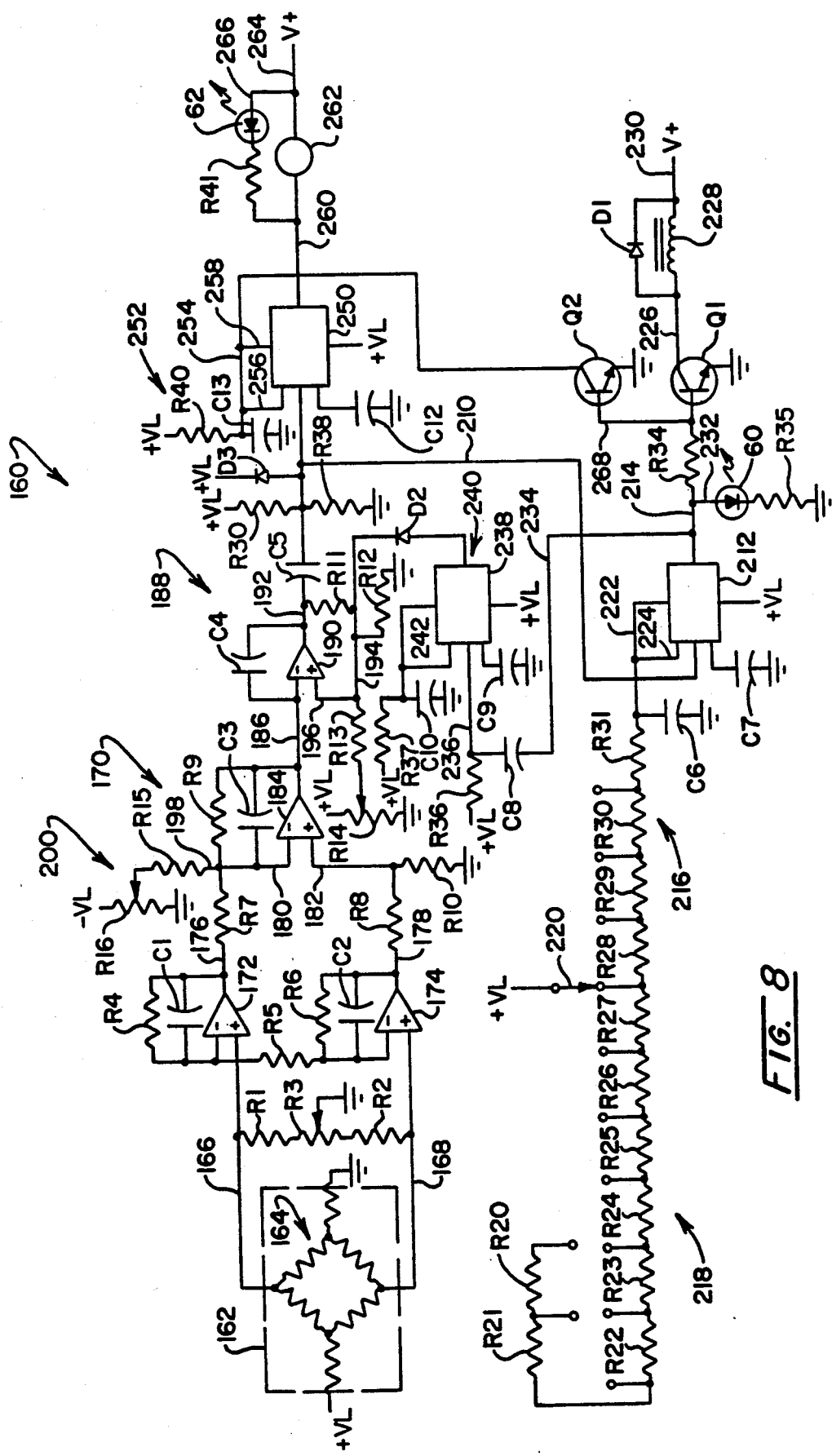
FIG. 8 is an electrical schematic diagram showing control components of the apparatus of the invention.

Referring to FIG. 8, a control circuit configured for carrying out the functions of the respiratory based delivery system of the invention is revealed generally at 160. As is somewhat conventional for pulsed based systems, the circuit 160 employs a diaphragm actuated pressure sensor (nanometer) represented within dashed boundary 162. Connected to respond to negative pressure developed during the inhalation phase of breathing, device 162 employs a wheatstone bridge resistor configuration which is exemplified at 164 to cause its output lines as at 166 and 168 to transition from a voltage balance to a voltage unbalance. Device 162 may be provided, for example, as a type SCX01 precision compensated pressure sensor marketed by SenSym, Inc. In order for the circuit 160 to respond to the inhalation of a patient with a very high degree of sensitivity, it is necessary that the sensor 162 remain balanced when under a rest or non-breathing condition. Accordingly, a factory adjusted balancing feature is employed between lines 166 and 168 which includes resistors R1 and R2 in combination with variable or adjustable resistor R3. The negative pressure responsive output, of device 162, when evidenced at lines 166 and 168 is amplified to a substantial extent, i.e. by a factor of 5,000, by a differential amplification network represented generally 170. The initial stage of amplification network 170 is formed of two very stable low-offset, low-power operational amplifiers 172 and 174. Output line 166 may be observed to be coupled with the non-inverting input of device 172, while output line 168 is similarly coupled with device 174. The outputs of amplifiers 172 and 174 shown respectively at lines 176 and 178 are coupled to feedback paths, respectively incorporating oscillation limiting capcacitors C1 and C2. The gain, for example 50, for this initial stage is established by resistors R4, R5, and R6. Devices 172 and 174 may be provided, for example, as type OP-400 operational amplifiers marketed by Precision Monolithics, Inc. The outputs of amplifiers 172 and 174, at respective lines 176 and 178 are directed through respective resistors R7 and R8 to lines 180 and 182. Lines 180 and 182 are directed, in turn, to the respective inverting and non-inverting inputs of operational amplifier 184. Amplifier 184, which also may be provided as a type OP-400 provides an output at line 186 and incorporates a feedback path including an oscillation controlling capacitor C3 and resistor R9. The gain of the stage represented at device 184 is about 100 and is established by the combination of resistors R9 and R7 as well as R10 and R8. The negative pressure responsive output which is now precision amplified at the very high gain of 5,000 is directed to the input of a comparator stage represented generally at 188. Stage 188 is comprised of an operational amplifier which may be provided as the earlier-noted type OP-400. The output of amplifier 190 is provided at line 192 and an oscillation controlling capacitor C4 is seen coupled between output line 192 and line 186 which is directed to an inverting input thereof. Stage 188 is configured with a Schmitt trigger characteristic, incorporating a variable form of hysteresis with respect to its trigger point or threshold. Hysteresis is developed from resistors R11 and R12 which are seen coupled to line 194, extending, in turn, through line 196 to the non-inverting input of amplifier 190. The bias or stand-by resting voltage level at line 196 at the non-inverting input to device 190 is established by resistor R13 and variable resistor R14. Factory adjustment carried out with variable resistor R14 provides that the voltage at line 196, or the non-inverting input to comparator stage 188, when at rest, is higher than the corresponding resting or stand-by voltage at the inverting input of device 190. This maintains the comparator stage 188 in a non-triggered state.

The occasion of a patient inhalation, the detection thereof by device 162 and amplification thereof at stage 170 will cause the output at line 186 to go positive or increase and, once the value thereof exceeds the voltage at the non-inverting input of stage 188, the output thereof at line 192 transistions to a logic negative level. That transition causes the triggering of a variety of components of the circuit 160.

Returning to amplification stage 170, it may be observed that line 176 is tapped intermediate resistors R7 and R9 by a lien 198 incorporating a resistor R15 which extends, in turn, as a wiper arm to a variable resistor or potentiometer R16. The latter resistor R16 is seen coupled between source $V_L$ and ground. This combination of components represents a user adjustable fine balance control or sensitivity adjustment discussed in conjunction with knob 52 in FIG. 1. Because a signal of relatively minute extent is developed from the sensing device 162 and is, subsequently, substantially amplified at stage 170, the unbalance signal from device 162 may be observed to drift over time or with temperature variation. This is conventionally accommodated for by diminishing the sensitivity of the system, in turn, requiring the patient to breathe with more effort in order to achieve an oxygen generating response. The sensitivity of the device 162 also may be affected by the geographic region in which it is used. For example, while a high level of sensitivity might be witnessed at a coastal region, where the devices than are used in a mountainous high altitude region, the sensitivity necessarily will diminish. The sensitivity adjustment stage, represented generally at 200, provides a user input by selectively biasing the resting level as desired which is ultimately witnessed at line 186. Thus, no matter what the conditions or extent of use of the circuit 160, the user has the capability of maintaining a high degree of sensitivity to the pulmonary process of inhalation.

Returning now to the output of comparator stage 188 at line 192, as noted above, with a negative going signal at that line representing the commencement of inspiration on the part of the patient, the resultant signal is coupled through capacitor C5 and line 210 to the trigger input of a timer 212. Provided, for example, as a type LM555 marketed by National Semi-Conductor Corporation, the timer 212 provides a pulse output at line 214, the duration of which is selected by an RC network 216 including capacitor C6 and a resistor ladder 218 comprised of resistors R20–R31. A capacitor, C7 is called for with a configuration of device 212. Resistors R20–R31 are of equal resistance value and are selected in switching fashion as represented by selector line 220. Line 220 is manually controlled from medical gas quantity selector knob 54 as described in connection with FIG. 1. In general, the selection thereat will be the equivalent of half liter increments of flow rates designated as liters per minute. Input from network 216 is directed via line 222 and 224 to the threshold input of device 212. Line 222 additionally extends to the discharge input of device 212 to provide for resetting network 216 following the generation of an output pulse at line 214. This pulse at line 214 is directed through base resistor R34 to the base of an NPN transistor Q1. Providing a driving function, the transistor Q1 may be provided, for example, as a type 2N4923 marketed by Motorola Corporation and is configured having its emitter coupled to ground and its collector coupled through line 226 to one side of the winding 228 of a solenoid actuated valve as described earlier in conjunction with FIG. 4 at 108. The opposite side of winding 228 is coupled via line 230 to supply V+ and a diode D1 is seen coupled across winding 228 to provide for reverse EMF suppression. Thus configured, the pulse applied to the base of transistor Q1 turns it on to, in turn, energize winding 228 and commence the development of a pulse of medical gas. The same signal at line 214 functions to illuminate a light emitting diode 60 described earlier in connection with FIG. 1 which is seen coupled within line 232 and through a resistor R35 to ground. Light emitting diode 60, as indicated earlier, provides a visual cue to the patient that a pulse of oxygen is under way.

It may be recalled that the control arrangement of the system 10 provides for the application of additional pulses of oxygen following an interval of six-tenths of a second subsequent to the completion of a first or last developed pulse. This timing feature is combined in the circuit 160 with a suppression feature designed to avoid the erratic performance of pulsing devices otherwise occasioned by pneumatic transients which occur following the generation of a pulse. These transient phenomena will tend to cause the sensing device 162 to react erratically false signals causing retriggering of the system, a condition sometimes referred to as "autopulsing". Such transient phenomena are avoided with the circuit 160. It may be observed that the output of timer 212 also is directed from output line 214 through line 234 and coupling capacitor C8 to line 236 and thence to the trigger input of a timer 238 of a timing and suppression network represented generally at 240. A resistor R36 is seen coupled to line 236 and to $+V_L$. Timer 238 may be provided, for example, as a type LM555 marketed by National Semi-Conductor Corporation. The CV port of the device is coupled through capacitor C9 to ground and the 0.6 second time-out of the device is developed by an RC network including capacitor C10 and resistor R37. In this regard, the timing network is coupled via lines 242 and 244 to the threshold input of device 238 and capacitor C10 is reset to initial value by virtue of the connection of line 242 to the discharge port of device 238. Device 238 is triggered by the negative going side of the pulse generated at line 214, and thus commences the noted 0.6 second time-out following the completion of a pulse forming energization of winding 228 of solenoid valve 108 (FIG. 4). When so triggered, a positive going pulse is generated at output line 246 which is directed through diode D2 to line 194 of the resistor network establishing the voltage level at the non-inverting input of device 190 of comparator network 188. With the suppression action, approximately 5 volts are directed through blocking diode D2 to establish the non-inverting input to operational amplifier 190 at a higher voltage than may be established in its inverting input from line 186. As a consequence, comparator stage 188 is effectively locked out of operation until the timeout established at timer 238 of the suppression network 240. Pneumatic transients within the system can have no effect upon the comparator stage 188. During the 0.6 second time-out, the inverting input to operational amplifier 190 is permitted to stabilize and, following such time-out, the non-inverting input of device 190 returns to its normal condition. If no negative pressure is sensed by device 162, indicating a continuation or presence of inhalation, then no further pulses are generated. However, with the ANDing logic of that negative pressure determination and the completion of the 0.6 second time-out generated by timer 238, a next pulse of oxygen will be generated in the manner described above.

The triggering pulse generated at line 192 also is directed to the trigger input of a timer 250. Resistors R38 and R39, coupled, respectively between ground and $+V_1$ serve to set a bias level above the trigger point of device 250, and capacitor C12 is coupled as required to the CV port terminal of device 250. A diode D3 additionally is coupled between line 192 and $+V_1$ for the purpose of positive spike suppression.

Timer 250 functions to develop the timing interval selected for generating an apnea alarm which is manifested both through the energization of a light emitting diode such as at 62 as described in conjunction with FIG. 1, as well as a piezoelectric sound making implement. The 70 second interval is timed by an RC network 252 comprised of capacitor C13 and resistor R40. As before, the network 252 is coupled to the threshold input of device 250 through lines 254 and 256 and the discharge terminal of the device is coupled to line 254 through line 258. The output of timer 250 at line 260 is seen directed to one side of a piezoelectric sound generating device 262, the opposite side of which is coupled via line 264 to V+ and about which light emitting diode 62 is coupled in serial associated with resistor R41 and line 266.

To provide assurance that the network 252 is reset at the commencement of its time-out, line 254 is seen directed to the collector electrode of an NPN transistor Q2, the emitter of which is coupled to ground and the base of which is coupled via line 268 to line 214. Transistor Q2 may be provided, for example, as a type 2N3904 marketed by Texas Instruments, Inc. The transistor is turned on with the commencement of a pulse generated from timer 212.

Figure 9:
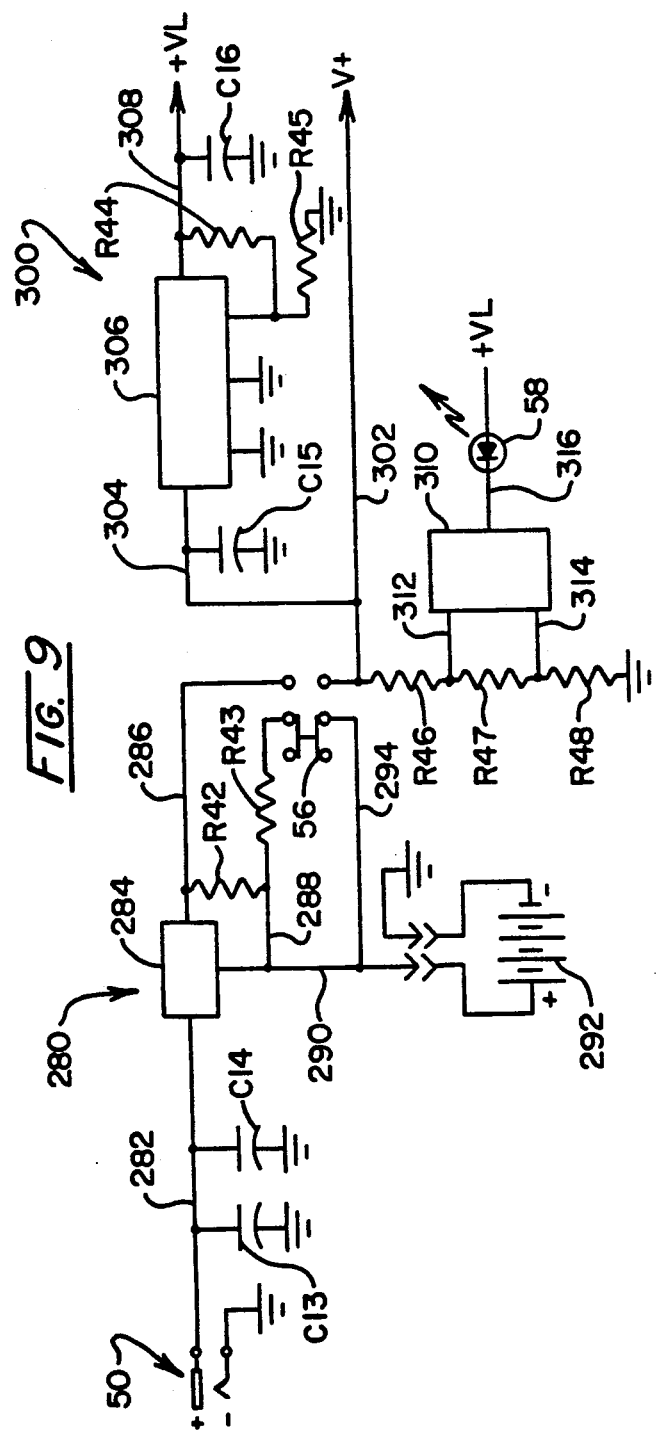
FIG. 9 is an electrical schematic diagram showing a battery charging and voltage regulation features of the control components of the invention.

Because of the extreme sensitivity of the amplification stage 170 and comparator stage 188, a voltage regulation of the power supply is necessitated to maintain the stability of the set points of circuit 160. Additionally, such regulation is desired for preventing re-triggering of the timers resulting in a chattering or machine-gunning effect. Referring to FIG. 9, an initial regulator and battery charging circuit is represented generally at 280. The circuit 280 is connectable with an external power supply through a jack input earlier described in connection with FIG. 1 at 50 and identified by the same numeration herein. One side of the jack 50 is coupled to ground and the other side is coupled via line 282 to the input terminal of a regulator 284. Capacitors C13 and C14 are coupled between line 282 and ground for providing a filtering function. Regulator 284 is an adjustable three-terminal positive voltage regulator which is capable of supplying 100 mA (constant current) over a 1.2 v to 37 v output range. Its output voltage at line 286 is established by resistors R42 and R43. In this regard, resistor R43 is seen connected between a switch earlier described at 56 in connection with FIG. 1, line 288, and 290, extending to the adjust terminal of device 284. Network 280 functions in conjunction with a rechargeable NiCd battery of nominal 6 v rating shown at 292. The positive terminal of battery 292 is seen connectable with line 290 from the output line 286 of regulator 284 and, additionally, is seen coupled through line 290 to line 294 extending to one side of switch 56. The negative terminal of battery 292 is shown connectable through line 296 to ground. With the off orientation of switch 56 shown, a constant charge of about 25 mA will be applied to battery 292 through regulator 284 and resistor R42.

In general, the network 280 is structured with the design assumptions that a 50% duty cycle of the operation of solenoid winding 228 will be present (FIG. 8), and a nominal draw of about 100 milliamps will be seen as a maximum consumption. With switch 56 in an on orientation, the constant current source represented by regulator 284 provides about 50 milliamps into the battery and into the general supply circuit via resistors R42 and R43 which are in parallel relationship with the switch in such on orientation. The 50 milliamps is sufficient to maintain the battery in a steady state of charge inasmuch as the battery 292 is supplying the second 50 milliamps required in the event of a 100 milliamp draw occasioned with the energization of winding 228. At the conclusion of an energizing pulse to solenoid winding 228, the 50 milliamps otherwise diverted to it is directed to battery 292 in a charging mode. Thus, a highly efficient charging activity is provided with respect to the performance of battery 292.

When switch 56 is closed, a second stage of regulation represented generally at 300 is activated. In this regard, line 294 will be coupled with line 302 of stage 300 which, in turn, is coupled via line 304 to a low drop-out regulator 306. Regulator 306 exhibits a very low voltage drop and will operate in conjunction with quite low voltage inputs. The device may be provided, for example, as a type LM2931 regulator marketed by National Semi-Conductor Corp. The regulator provides an output at line 308 for input to the logic components of circuit 160 and is labeled $+V_L$. Regulator 306 is configured in conventional fashion in conjunction with capacitors C15 and C16 as well as resistors R44 and R45.

A low battery condition is sensed by a voltage detector 310, the level of which is set by resistor string R46-R48 coupled between ground and line 302. Device 310 may, for example, be provided as a type ICL8211 programmable voltage detector marketed by the Intersil Division of General Electric Company. The hysteresis terminal of device 310 is coupled intermediate resistors R46 and R47 via line 312, while the threshold terminal thereof is coupled intermediate resistors R47 and R48. The output of device 310 at line 316 is connected to one side of light emitting diode 58, the opposite side of which is coupled to $+V_L$. Diode 58 provides the low battery indication as described in conjunction with FIG. 1.

Since certain changes may be made in the above-described apparatus and method without departing from the scope of the invention herein involved, it is intended that all matter contained in the description thereof or shown in the accompanying drawings shall be interpreted as illustrative and not in a limiting sense.

We claim:

1. The method for supplying medical gas to the respiratory system of a patient during the course of a given cycle of inhalation and exhalation comprising the steps of:
    providing a supply of said gas under regulated pressure;
    providing a gas conduit input positionable upon said patient and responsive to the instantaneous pressures of said patient respiratory system to exhibit at negatively categorized pressure upon a said inhalation of a said given cycle;
    detecting the commencement of said negatively categorized pressure during said given cycle;
    providing a first pulse supply of predetermined duration of said gas to said patient in a quantity corresponding with a select gas application rate, substantially at said detected commencement of negatively categorized pressure; and
    providing a second pulse supply of predetermined duration of said gas to said patient in the presence of said negatively categorized pressure during said given cycle and following a first predetermined delay interval.

2. The method of claim 1 including the step of providing a third pulse supply of said gas of predetermined duration to said patient in the presence of said negatively categorized pressure during said given cycle and following a second predetermined interval subsequent to said first predetermined interval.

3. The method of claim 2 in which said predetermined duration of said third pulse supply of said gas is substantially the same as said predetermined duration of said first pulse supply of gas.

4. The method of claim 1 in which said select gas application rate is a rate prescribed for said patient when in a state of rest.

5. The method of claim 1 in which said predetermined duration of said second pulse supply of said gas is substantially the same as said predetermined duration of said first pulse supply of gas.

6. The method of claim 1 in which said first and second pulse supplies of said gas are generated by the actuation of a valve in a manner deriving an open and close time of rapidity effective to generate a physical perception of said first and second pulse by said patient.

7. The method of claim 1 in which said first and second pulse supplies of said gas are generated in conjunction with an acoustic output for audible perception by said patient.

8. The method of claim 1 in which said first predetermined delay interval is about 0.6 second.

9. The method of claim 1 in which said predetermined duration of said first and second pulse supplies of said gas are at least about 128 ms.

10. The method of claim 1 including the step of providing a visually perceptible cue to said patient in correspondence with the provision of said first and second pulse supply of said gas.

11. Apparatus for administering medical gas from a source thereof to the respiratory tract of a patient in the course of a cycle of inhalation and exhalation and in correspondence with a select application rate, comprising:
    a medical gas circuit connectable with said source and having a gas application valve actuable for a pulse forming interval to apply said medical gas to said patient through an application conduit conveying an inhalation and expiration pressure condition of said patient;

a pressure sensor coupled with said medical gas circuit and having a sensing output in response to the said presence of a said inhalation pressure condition through said application conduit for said cycle;

an amplifier responsive to said sensing output for deriving an amplified sensing signal;

a comparator responsive to a threshold input of predetermined level and to said amplified sensing signal for deriving a triggering output in correspondence with said inhalation pressure condition;

a pulse timer responsive to said triggering output for deriving a pulse output of select duration for effecting said actuation of said gas application valve for said select duration; and next pulse timing means responsive to said pulse output for effecting the derivation of said triggering output a predetermined interval subsequent to said pulse output in the continued and uninterrupted presence of said sensing output representing said inhalation during said cycle.

12. The apparatus of claim 11 in which said next pulse timing means is responsive at the termination of said pulse timer output of select duration to suppress the generation of said triggering output for said predetermined interval.

13. The apparatus of claim 11 in which said next pulse timing means is responsive at the termination of said pulse timer output of select duration to alter said threshold to a level varying from said predetermined level an extent effecting the suppression of said derivation of said triggering output for said predetermined interval.

14. The apparatus of claim 11 in which said amplifier is a dual stage differential amplifier having a gain of about 5000.

15. The apparatus of claim 11 including:
an apnea alarm energizable to provide a perceptible output; and
an apnea timer responsive to one said triggering output for energizing said apnea alarm at the termination of a predetermined apnea interval in the absence of the occurrence of a next said triggering output subsequent to said one triggering output within said predetermined apnea interval.

16. The apparatus of claim 11 in which:
said medical gas circuit includes a conduit path extending from said application conduit to said pressure sensor;
said gas application valve is operatively associated with said conduit path between said pressure sensor and said patient; and
including a check valve within said conduit path between said gas application valve and said pressure sensor and configured for restricting response of said pressure sensor to only negative inhalation gas pressures.

17. The apparatus of claim 11 in which said pulse timer includes a resistor array; a capacitor selectively connectable therewith to form a timing network; manually actuable switch means for coupling select ones of resistors of said array with said capacitor to define said pulse output of select duration corresponding with said select application rate.

18. The apparatus of claim 11 in which:
said amplifier has an output of first standby level and responsive to said sensing output to alter said standby level to said amplified signal; and
including a sensitivity adjustment network manually adjustable to vary said amplifier standby level away from or towards said comparator threshold level.

19. The apparatus of claim 18 in which:
said pressure sensor includes a diaphragm actuated electrical bridge having first and second balanced standby outputs in the absence of said pressure condition and deriving said sensing output as first and second unbalanced sensing outputs in response to said pressure condition; and
including an adjustable balancing network coupled with said pressure sensor for establishing said first and second balanced standby outputs.

20. The apparatus of claim 18 in which said amplifier is a differential amplifier having a gain of about 5000.

21. The apparatus of claim 18 including next pulse timing means responsive to said pulse output for effecting the derivation of said triggering output a predetermined interval subsequent to said pulse output when said amplified sensing signal continues to exceed said comparator threshold level.

22. The apparatus of claim 11 including:
signal suppression means responsive at the termination of said pulse output of select duration to suppress the generation of said triggering output for a predetermined interval, so as to avoid the generation of a false triggering output due to pneumatic transients.

23. Apparatus for administering medical gas from a source thereof at source pressure to the respiratory tract of a patient comprising:
a solenoid valve having a winding energizable to assume a gas transfer orientation from a closed orientation;
a first gas transfer path connectable with said source and in gas transfer relationship with said solenoid valve;
a bypass valve manually adjustable from a closed position to provide select gas flow rates;
a second gas transfer path connectable with said source and in gas transfer relationship with said bypass valve;
a third gas path connected in gas transfer relationship to said bypass valve and said solenoid valve and operably associated with said patient respiratory tract;
a variable area gas flow meter including a transparent tubular housing, a ball therein responsive in gas buoyancy to fluid flow through said housing, and gas flow rate indicia upon said housing, coupled within said second gas transfer path; and
control means for selectively energizing said solenoid winding.

24. The apparatus of claim 23 including manually actuable pressure reduction valve means coupled within said first gas transfer path for selectively reducing said source pressure.

25. The method for supplying medical gas to the respiratory system of a patient during the course of inhalation and exhalation comprising the steps of:
providing a supply of said gas under regulated pressure;
providing a gas conduit input positionable upon said patient and responsive to the instantaneous pressures of said patient respiratory system to exhibit a negatively categorized pressure upon said inhalation;

detecting the commencement of said negatively categorized pressure;

providing a first pulse supply of predetermined duration of said gas to said patient in a quantity corresponding with a select gas application rate, substantially at said detected commencement of negatively categorized pressure; and providing a second pulse supply of predetermined duration of said gas to said patient in the presence of said negatively categorized pressure and following a first predetermined delay interval of about 0.6 second.

26. The method for supplying medical gas to the respiratory system of a patient during the course of inhalation and exhalation comprising the steps of:

providing a supply of said gas under regulated pressure;

providing a gas conduit input positionable upon said patient and responsive to the instantaneous pressures of said patient respiratory system to exhibit a negatively categorized pressure upon said inhalation;

detecting the commencement of said negatively categorized pressure;

providing a first pulse supply of predetermined duration of said gas to said patient in a quantity corresponding with a select gas application rate, substantially at said detected commencement of negatively categorized pressure;

providing a second pulse supply of predetermined duration of said gas to said patient in the presence of said negatively categorized pressure and following a first predetermined delay interval; and providing a third pulse supply of said gas of predetermined duration to said patient in the presence of said negatively categorized pressure and following a second interval of about 0.6 second subsequent to said first predetermined interval.

27. Apparatus for administering medical gas from a source thereof to the respiratory tract of a patient in correspondence with a select application rate, comprising:

a medical gas circuit connectable with said source and having a gas application valve actuable for a pulse forming interval to apply said medical gas to said patient through an application conduit conveying an inhalation and expiration pressure condition of said patient;

a pressure sensor coupled with said medical gas circuit and having a sensing output in response to the said presence of a said inhalation pressure condition through said application conduit;

an amplifier responsive to said sensing output for deriving an amplified sensing signal;

a comparator responsive to a threshold input of predetermined level and to said amplified sensing signal for deriving a triggering output in correspondence with said inhalation pressure condition;

a pulse timer responsive to said triggering output for deriving a pulse output of select duration for effecting said actuation of said gas application valve for said select duration; and next pulse timing means responsive to said pulse output for effecting the derivation of said triggering output an interval of about 0.6 seconds subsequent to said pulse output in the presence of said sensing output.

28. Apparatus for administering medical gas from a source thereof to the respiratory tract of a patient in correspondence with a select application rate, comprising:

a medical gas circuit connectable with said source and having a gas application valve actuable for a pulse forming interval to apply said medical gas to said patient through an application conduit conveying an inhalation and expiration pressure condition of said patient;

a pressure sensor coupled with said medical gas circuit and having a sensing output in response to the said presence of a said inhalation pressure condition through said application conduit;

said medical gas circuit including a conduit path extending from said application conduit to said pressure sensor;

said gas application valve being operatively associated with said conduit path between said pressure sensor and said patient;

a check valve within said conduit path between said gas application valve and said pressure sensor and configured for restricting response of said pressure sensor to only negative inhalation gas pressures;

an amplifier responsive to said sensing output for deriving an amplified sensing signal;

a comparator responsive to a threshold input of predetermined level and to said amplified sensing signal for deriving a triggering output in correspondence with said inhalation pressure condition;

a pulse timer responsive to said triggering output for deriving a pulse output of select duration for effecting said actuation of said gas application valve for said select duration; and next pulse timing means responsive to said pulse output for effecting the derivation of said triggering output a predetermined interval subsequent to said pulse output in the presence of said sensing output.

29. Apparatus for administering medical gas from a source thereof at source pressure to the respiratory tract of a patient comprising:

a solenoid valve having a winding energizable to assure a gas transfer orientation from a closed orientation;

a first gas transfer path connectable with said source and in gas transfer relationship with said valve;

a bypass valve manually adjustable to provide select gas flow rates;

a second gas transfer path connectable with said source and in gas transfer relationship with said bypass valve;

a third gas path connected in gas transfer relationship to said bypass valve and said solenoid valve and operably associated with said patient respiratory tract;

a check valve within said third gas transfer path for effecting conveyance of said negative pressures to said gas pressure sensor and blocking conveyance of positive gas pressures thereto;

a variable area gas flow meter including a transparent tubular housing, a ball therein responsive in gas buoyancy to fluid flow through said housing, and gas flow rate indicia upon said housing, coupled within said second gas transfer path; and control mean for selective energizing said solenoid winding and including a gas pressure sensor coupled with said third gas transfer path and responsive to negative pressures therein to effect energization of said solenoid winding.

* * * * *